United States Patent
Shi

(10) Patent No.: US 6,384,265 B1
(45) Date of Patent: May 7, 2002

(54) METHODS FOR PRODUCING α-ACYLOXY CARBONYL COMPOUNDS FROM ENOL ESTER EPOXIDES

(75) Inventor: Yian Shi, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/534,419

(22) Filed: Mar. 23, 2000

Related U.S. Application Data

(60) Provisional application No. 60/125,687, filed on Mar. 23, 1999.

(51) Int. Cl.$^7$ .............................................. C07C 69/76
(52) U.S. Cl. ....................................... 560/106; 560/103
(58) Field of Search .................................. 560/106, 103

(56) References Cited

U.S. PATENT DOCUMENTS 4,902,820 A   2/1990   Zoeller ........................ 560/185

OTHER PUBLICATIONS

Williamson et al., "Acid–catalyzed–rearrangement of enol ester epoxide" in J.Org.Chem. 1967,32(12), 3934–7.*
Adam et al., "Synthesis of Optically Active alpha–Hydroxy Carbonyl Compounds by the Catalytic, Enantioselective Oxidation of Silyl Enol Ethers and Ketene Acetals with (Salen)manganese(III) Complexes" in J. Am. Chem. Soc. 1998, 120, 708–714.*
Richard N. McDonald, *Mech., Mol. Migr.*, 1971, 3, 67.
A. H. Soloway et al., *J. Am. Chem. Soc.*, 1954, 76, 2941.
Norma S. Leeds et al., *J. Am. Chem, Soc.*, 1954,76,2943.
Pete D. Gardner, *J. Am, Chem. Soc.*, 1956 3421.
William S. Johnson, *J. Am, Chem, Soc.*, 1957, 79, 1991.
H. J. Shine et al., *J. Am. Chem. Soc.*, 1958, 80, 2434.
Herbert O. House et al., *J.Org. Chem.*, 1961, 26,3729.
J. Attenburrow et al., *J. Am. Chem. Coc.*, 1961, 26, 4563.
Kenneth L. Williamson et al. *J. Org. /Chem.*, 1961, 4563.
Toshio Nambara et al., *Bull. Soc. Chim. Fr.*, 1963, 224.
James R. Rhone, *Tetrahedron Lett.*, 1965, 1395.
Kenneth L. Williamson et al.,*J. Org. Chem.*, 1967, 32, 3934.
Stehpen C. Smith et al.,*J. Org. Chem.*, 1992, 57,6379.
Yuanming Zhu et al., *J. Org. Chem. Soc.*, 1999, 121, 4080.
Xiaoming Feng et al.,*J. Am. Chem. Soc.*, 1999, 121, 11002.
Yuanming Zhu *J. Org. Chem.*, 2001, 66, 1818.
A. L. Draper et al., *J Org. Chem*1962, 27, 2727.
Jean–Jacques Riehl et al., *Bull. Soc. Chim. Fr.*, 1963, 224.
Richard N. McDonald et al., *J. Am. Chem. Soc.*, 1967, 89, 6573.

* cited by examiner

*Primary Examiner*—Ralph Gitomer
*Assistant Examiner*—Devesh Khare
(74) *Attorney, Agent, or Firm*—Townsend and Townsend and Crew LLP

(57) ABSTRACT

The present invention provides a method for producing an α-acyloxy carbonyl compound from an enol ester epoxide stereoselectively using an acid catalyst which is capable of affecting rearrangement of the enol ester epoxide with inversion of stereochemistry. The present invention also provides a method for kinetic resolution of a stereoisomeric mixture of enol ester epoxides using a chiral catalyst. The kinetic resolution generally involves stereoselectively producing one particular enantiomer of α-acyloxy carbonyl compounds from the stereoisomeric mixture of enol ester epoxides.

26 Claims, No Drawings

METHODS FOR PRODUCING α-ACYLOXY CARBONYL COMPOUNDS FROM ENOL ESTER EPOXIDES

CROSS-REFERENCE TO RELATED APPLICATIONS

This application claims the benefit of U.S. Provisional Application Ser. No. 60/125,687, filed Mar. 23, 1999, which is incorporated herein by reference in its entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant Nos. GM55704-01 and GM59705-01, both of which were awarded by National Institute of Health.

FIELD OF THE INVENTION

The present invention is directed to kinetic resolution of enol ester epoxides and to production of α-acyloxy carbonyl compounds from enol ester epoxides, in particular with inversion of stereochemistry.

BACKGROUND OF THE INVENTION

The stereochemistry of a molecule is important in many of the properties of the molecule. For example, it is well known that physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer. Thus, it is advantageous to be able to control the stereochemistry of a chemical reaction or to be able to separate or enrich stereoisomers of a compound from a mixture.

Epoxides are used in many industrial processes as chiral building blocks for the synthesis of enantiomerically pure complex molecules such as polymers, surfactants, pesticides, insecticides, insect hormones, insect repellants, pheromones, food flavoring, and drugs. One can stereoselectively synthesize a variety of chiral epoxides, for example, as disclosed in commonly assigned PCT Patent Application No. PCT/US97/18310, filed Oct. 8, 1997, which is incorporated herein by reference in their entirety. However, there are instances where such asymmetric synthesis of epoxides may not be possible or economically desirable or cost effective. Since an epoxide serves as an intermediate or a starting material for many chemical compounds, it is especially desirable to have a general method for resolving a racemic mixture of epoxides or be able to stereoselectively convert one particular stereoisomer of the epoxide to afford enantiomerically enriched products and/or unreacted epoxides.

One of the useful products derived from an enol ester epoxide is an α-acyloxy carbonyl compound. Enol ester epoxides can rearrange to α-acyloxy ketones or aldehydes under a variety of conditions, for example, thermal or acidic conditions. An α-acyloxy carbonyl compound itself can be further used as a chiral building block in many industrial processes. While a variety of reagents are available for converting enol ester epoxides to α-acyloxy carbonyl compound with retention of stereochemistry, currently no acid catalyzed method is available for stereoselectively converting enol ester epoxides to α-acyloxy carbonyl compound with inversion of stereochemistry.

Therefore, there is a need for a method for converting enol ester epoxides to α-acyloxy carbonyl compounds with inversion of stereochemistry. There is also a need for a method for resolving a racemic or stereoisomeric mixture of enol ester epoxides.

SUMMARY OF THE INVENTION

The present invention provides a method for stereoselectively producing an α-acyloxy carbonyl compound from an enol ester epoxide comprising contacting the enol ester epoxide with an acid catalyst under a condition sufficient to stereoselectively produce the α-acyloxy carbonyl compound. Preferably, the conversion of enol ester epoxide to the α-acyloxy carbonyl compound includes an inversion of stereochemistry. When the enol ester epoxide is enantiomerically enriched, an achiral catalyst can be used to stereoselectively convert the enol ester epoxide to either of the desired α-acyloxy carbonyl compound stereoisomers.

Alternatively, a chiral Lewis acid catalyst can be used to provide a kinetic resolution of the racemic mixture of enol ester epoxides. By combining these two processes (e.g., the use of a chiral Lewis acid followed by the use of an achiral acid catalyst), a stereoselective production of predominantly one stereoisomer of α-acyloxy carbonyl compounds from both stereoisomers of enol ester epoxides can be achieved from a racemic mixture of enol ester epoxides.

Another embodiment of the present invention provides a kinetic resolution of a stereoisomeric mixture of an enol ester epoxide. Preferably, the kinetic resolution of enol ester epoxide involves contacting the stereochemical mixture (i.e., stereoisomeric mixture) of the enol ester epoxide with a chiral Lewis acid catalyst to convert predominantly one enantiomer of the enol ester epoxide to an α-acyloxy carbonyl compound. Preferably, the chiral Lewis acid catalyst stereoselectively converts the enol ester epoxide to the α-acyloxy carbonyl compound.

DETAILED DESCRIPTION OF THE INVENTION

As used herein, the terms "inversion" and "inversion of stereochemistry" are used interchangeably herein and refer to a process which results in the α-acyloxy group of the α-acyloxy carbonyl compound having an opposite stereochemical configuration relative to the stereochemistry of the starting epoxide group. This is generally illustrated in the conversion of compound 3 to compound 8 in Scheme 1 below. Preferably, when methods of the present invention result in inversion of stereochemistry at least about 75% of the product results from inversion of stereochemistry, more preferably at least about 80%, still more preferably at least about 90%, yet still more preferably at least about 95%, and most preferably substantially all of the product has inversion of stereochemistry.

The terms "retention" and "retention of stereochemistry" are used interchangeably herein and refer to a process which results in the α-acyloxy group of the α-acyloxy carbonyl compound having a same stereochemical configuration relative to the stereochemistry of the starting epoxide group. This is generally illustrated in the conversion of compound 3 to compound 6 in Scheme 1 below. Preferably, when methods of the present invention result in retention of stereochemistry at least about 75% of the product results from retention of stereochemistry, more preferably at least about 80%, still more preferably at least about 90%, yet still more preferably at least about 95%, and most preferably at least about 99%.

The terms "enantioselective" and "stereoselective" are used interchangeably herein and refer to a process which results in the production of an α-acyloxy carbonyl compound having predominantly one particular stereochemistry of the α-acyloxy group. It should be appreciated that while the enol ester epoxide may have other chiral centers other than the epoxide moiety, the terms "enantioselective" and "stereoselective" refer only to the α-acyloxy stereochemical center resulting from the opening of the epoxide ring moiety.

The terms "enantiomeric excess" and "stereoisomeric excess" are used interchangeably herein and refer to a process which produces an α-acyloxy carbonyl compound having predominantly one particular stereochemistry of the α-acyloxy group. Preferably, methods of the present invention produce the α-acyloxy carbonyl compound, with inversion of the stereochemistry, in an enantiomeric excess of at least about 12% ee, more preferably at least about 80% ee, still more preferably at least about 90% ee, and most preferably at least about 95% ee.

Unless the context requires otherwise, the terms "stereoisomeric mixture" and "stereochemical mixture" are used interchangeably herein and refer to a relative ratio of each stereoisomer or enantiomer present in the starting material, e.g., prior to a kinetic resolution. Furthermore, when these terms are used without any value, they refer to the fact that the starting material contains more than one stereoisomer or enantiomer.

The term "enantiomerically enriched mixture" of a compound refers to a stereoisomeric or enantiomeric mixture of a compound where the relative ratio of each stereoisomer or enantiomer is different than the starting material, e.g., prior to a kinetic resolution.

An "enol ester epoxide" refers to an epoxide compound having an acyloxy substituent on one of the carbon atoms of the epoxide ring, i.e., a compound having the formula:

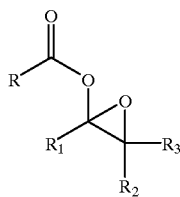

An "α-acyloxy carbonyl compound" refers to a carbonyl compound, e.g., a ketone or aldehyde, having an acyloxy substituent α to the carbonyl functionality, i.e., a compound having the formula:

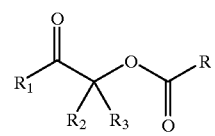

For the sake of brevity and clarity, $R_3$ in enol ester epoxide and α-acyloxy carbonyl compound is typically not illustrated hereinafter, but it is intended that this disclosure cover cases where $R_3$ is present.

The term "kinetic resolution" refers to a process or a method of increasing the concentration of one particular enantiomer or stereoisomer of enol ester epoxide. Such process is preferably affected by converting, i.e., transforming, one particular enol ester epoxide enantiomer or stereoisomer to a different compound, e.g., preferably α-acyloxy carbonyl compound, at a rate faster than conversion of the other enantiomer or stereoisomer.

The present invention provides a method for producing α-acyloxy carbonyl compounds from enol ester epoxides. Preferably, methods of the present invention involve inversion of stereochemistry. The enol ester epoxide can be a racemic mixture or an enantiomerically enriched mixture. When the enol ester epoxide is a racemic mixture, methods of the present invention can include a kinetic resolution of the enol ester epoxide by converting one particular stereoisomer of the enol ester epoxide to an α-acyloxy carbonyl compound at a rate faster than the other enol ester epoxide stereoisomer, preferably involving inversion of stereochemistry. This kinetic resolution results in production of enantiomerically enriched α-acyloxy carbonyl compound and enantiomerically enriched enol ester epoxide, i.e., unreacted enol ester epoxide. The enantiomerically enriched enol ester epoxide resulting from the kinetic resolution can be further converted to α-acyloxy carbonyl compound with retention of stereochemistry, thereby increasing the yield of the total α-acyloxy carbonyl compound with a desired stereochemistry. Alternatively, the resulting enantiomerically enriched enol ester epoxide can be separated and converted to the α-acyloxy carbonyl compound with inversion of stereochemistry; thus, allowing production of stereoisomerically enriched α-acyloxy carbonyl compound of both stereoisomers.

Production of a racemic mixture of enol ester epoxide is well known to one of ordinary skill in the art. And enantiomerically enriched enol ester epoxides can be readily produced, for example, using a fructose-derived ketone catalyst as disclosed by the present inventors in PCT Patent Application No. PCT/US97/18310, which is incorporated herein by reference in its entirety.

Methods of the present invention generally include contacting an enol ester epoxide with a catalyst, preferably an acid catalyst, under conditions sufficient to produce α-acyloxy carbonyl compound with inversion of stereochemistry. When the enol ester epoxide is a racemic mixture, preferably the catalyst is a Lewis acid comprising a chiral ligand. In particular, the Lewis acid comprises a metal. Preferably, the metal is selected from the group consisting of Al, B, Cs, Sn, transition metals, lanthanide metals, actinide metals, and mixtures thereof. More preferably, the metal is titanium.

A chiral ligand according to the invention are moieties which possess chiral centers and exert facial selectivity of a reaction based on their chirality. A chiral center is, of course, an atom to which four different groups are attached; however, the ultimate criterion of chiral center is nonsuperimposability on the mirror image. Facially selective or stereoselective synthetic reactions are those in which one of a set of stereoisomers is formed exclusively or predominantly. Preferably, one isomer is produced in 50% excess over the other isomers. More preferably, one isomer is produced in 80% excess over the other isomers. Still more preferably, one isomer is produced in 90% excess over the other isomers. Even more preferably, one isomer is produced in 95% excess over the other isomers. Any chiral ligands currently known in the art of synthetic organic chemistry may be used. Exemplary chiral ligands include BINOL, tartrate, and other chiral ligands which are used in a variety of organic reactions. In one particular embodiment of the present invention, BINOL is used as a chiral ligand. Preferably, the chiral ligand is selected from the group consisting of (R)-BINOL and (S)-BINOL.

The enantiomeric excess of the α-acyloxy carbonyl compound produced by methods of the present invention can vary depending on a variety of factors. For example, as Table 1 shows, a particular Lewis acid catalyst used in converting an enol ester epoxide can affect the enantiomeric excess of the resulting α-acyloxy carbonyl compound. Thus, while some acids such as p-TsOH, Sn(OTf)$_2$ and Yb(OTf)$_3$ provide high ee% of the retention product, other acids such as YbCl$_3$, ErCl$_3$, AlMe$_3$, AlEt$_2$Cl and silica gel provide high ee% of the inversion product.

TABLE 1

The Effects of Different Acid Catalysts on the
Rearrangement of 1-benzoyloxy-1,2-epoxycyclohexane(1)[a]

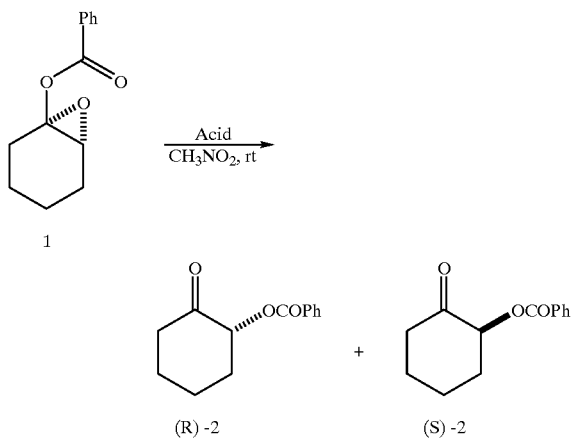

| entry | acid | t(min) | % ee(1)[b] | % ee(2)[b] | % yield[c] |
|---|---|---|---|---|---|
| 1 | p-TsOH | 10 | 93 | 90(R) | 89 |
| 2 | Sn(OTf)$_2$ | 10 | 93 | 85(R) | 84 |
| 3 | AlCl$_3$ | 1 | 92 | 26(R) | 74 |
| 4 | La(OTf)$_3$ | 40 | 93 | 15(R) | 88 |
| 5 | Yb(OTf)$_3$ | 5 | 92 | 66(R) | 67 |
| 6 | YbCl$_3$ | 90 | 93 | 82(S) | 76 |
| 7 | ZnBr$_2$ | 10 | 93 | 12(S) | 48 |
| 8 | ErCl$_3$ | 90 | 90 | 80(S) | 73 |
| 9 | AlMe$_3$ | 5 | 91 | 87(S) | 85 |
| 10 | AlEt$_2$Cl | 17 | 91 | 67(S) | 54 |
| 11 | AlEtCl$_2$ | 10 | 91 | 30(S) | 41 |
| 12 | Silica gel | 720 | 92 | 91(S) | 83 |

[a]All reactions were carried out in nitromethane under anhydrous conditions at room temperature using 10 mol % acid catalyst except entry 12 where 5–10 times (by weight) silica gel (Davisil 35-60 mesh, pH 7.0) was used. Epoxide 1 was freshly made and stored at −20° C. prior to use to avoid decomposition.
[b]The enantiomeric excess was determined by HPLC (Chiracel OD). The absolute configuration of 2 was determined by comparing HPLC chromatograms with the authentic sample prepared from commercially available (R,R)-1,2-trans-cyclohexanediol.
[c]Isolated yield.

A wide variety of Lewis acids can be used to convert an enol ester epoxide to an α-acyl carbonyl compound. There are many acid catalysts known to one of ordinary skill in the art which produce an α-acyl carbonyl compound from an enol ester epoxide with retention of stereochemistry.

The present invention is based on a surprising and unexpected discovery by the present inventors that, as shown in Table 1, some Lewis acid catalysts are capable of producing an α-acyl carbonyl compound from an enol ester epoxide with an inversion of stereochemistry, preferably with stereoselectivity. By utilizing the disclosure of the present invention, one of ordinary skill in the art can readily determine other Lewis acid catalysts which are capable of providing an inversion of stereochemistry during the rearrangement reaction. For example, one of ordinary skill in the art can use the reaction shown in Table 1 or in the Examples section to determine whether a particular acid catalyst is capable of converting an enol ester epoxide to an α-acyloxy carbonyl compound with inversion of stereochemistry. Thus, using an appropriate Lewis acid catalyst, an α-acyloxy carbonyl compound with an inversion of stereochemistry having an enantiomeric excess of at least about 12% ee can be obtained by the method of the present invention, preferably with an enantiomeric excess of at least about 80% ee, more preferably at least 90% ee, and most preferably at least about 95% ee.

Without being bound by any theory, Scheme 1 shows two possible pathways involved in the acid-catalyzed rearrangement of enol ester epoxides, thus leading to two different enantiomers.

Scheme 1

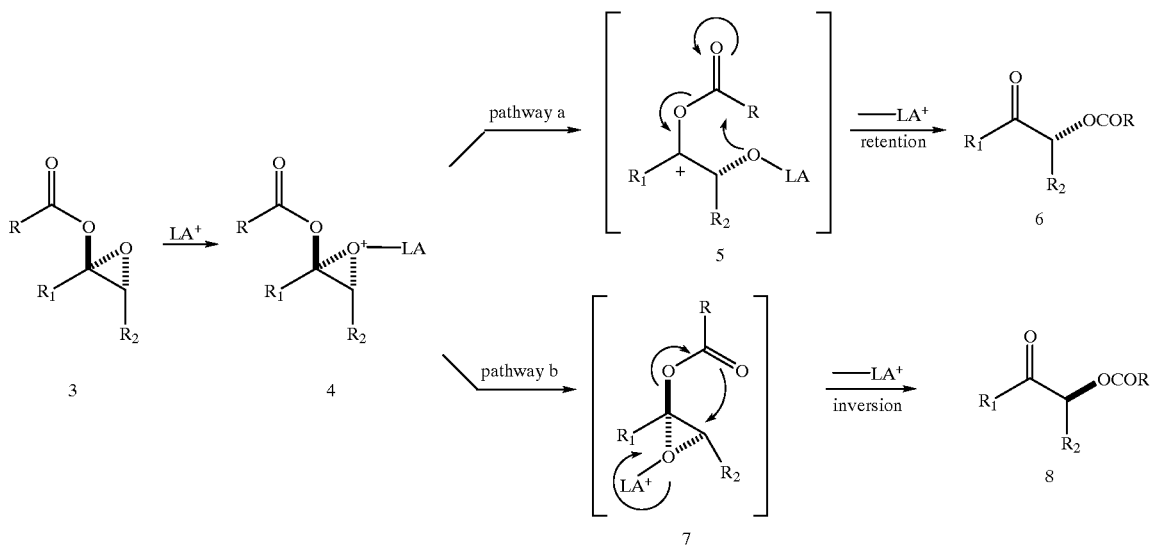

Pathways a and b outlined in Scheme 1 provide plausible mechanisms for the results. In pathway a, it is believed that the complexation of a relatively strong acid catalyst to the epoxide oxygen of 3 leads to cleavage of the $C_1$—O bond to form a carbocation intermediate 5. Subsequent acyl migration with retention of configuration gives acyloxy ketone 6. In pathway b, the complexation of a relatively weak acid to 3 weakens both epoxide bonds, facilitating acyloxy migration with inversion of configuration as shown in intermediate 7. Thus, it is believed that the acidity of the catalyst is one of the factors determining whether the catalyst is capable of producing an α-acyloxy carbonyl compound from an enol ester epoxide with inversion of stereochemistry. For example, as shown in Table 1, when $Yb(OTf)_3$ was used as the catalyst, the R enantiomer of the rearranged product was obtained in 66% ee (Table 1, entry 5), i.e., retention product predominates. On the other hand, when a weaker Lewis acid $YbCl_3$ was used, the S enantiomer was obtained in 82% ee (Table 1, entry 6), i.e., the product is predominantly derived from inversion of stereochemistry. In most cases, the enantiomeric excess of α-acyloxy carbonyl compound could be further enhanced, for example, by recrystallization.

The reaction temperature also can affect the stereoselectivity of rearrangement. Preferably, the reaction temperature of rearrangement is kept at about 25° C. or less, more preferably at about 10° C. or less, and most preferably at about 0° C. or less.

A wide variety of solvent system can be used to affect the stereoselective conversion of an enol ester epoxide to an α-acyloxy carbonyl compound. Exemplary solvents useful in the rearrangement include $CH_3NO_2$, $CH_2Cl_2$, $CHCl_3$, diethyl ether, benzene, tetrahydrofuran, dimethylformamide, toluene, xylenes, dimethylsulfoxide, acetonitrile, hexane, pentane, and mixtures thereof. Preferably the solvent is selected from the group consisting of nitromethane, methylene chloride and mixtures thereof.

The amount of catalyst used in conversion of enol ester epoxide to an α-acyloxy carbonyl compound depends on a variety of factors. Generally, however, from about 1 mole % to about 100 mole % of catalyst relative to the enol ester epoxide is used. Preferably from about 5 mole % to about 100 mole % of catalyst relative to the enol ester epoxide, more preferably from about 5 mole % to about 50 mole % of catalyst relative to the enol ester epoxide, and most preferably from about 5 mole % to about 10 mole % of catalyst relative to the enol ester epoxide.

The reaction time also depends on a variety of factors such as temperature and concentration of each components. Generally, however, the reaction time is from about 0.1 h to about 48 h, preferably from about 0.1 h to about 10 h, and more preferably from about 0.1 h to about 1 h.

As shown in Table 2, synthesis of either enantiomer of an α-acyloxy carbonyl compound from one enantiomer of an enol ester epoxide is possible by carefully selecting reaction conditions, e.g., by selecting a particular acid catalyst. To test the generality of the rearrangement via pathway b, silica gel, $YbCl_3$, and $AlMe_3$ were used (Table 2). In most cases the isomer with inverted configuration was the major product when silica gel, $YbCl_{13}$, and $AlMe_3$ are used as the catalyst; however, in two cases (Table 2, entries 6 and 7) the rearrangement proceeded with retention of configuration. The preference for pathway a with these benzylic epoxides is believed to be due to a stabilized carbocation intermediate 5.

TABLE 2

Examples of p-TsOH, Silica gel, YbCl₃, or AlMe₃ Catalyzed Rearrangements of Enol Ester Epoxides[a]

| entry | epoxide | acid | time (h) | epoxide % ee[d] | product ee (%)[e] | yield (%)[j] |
|---|---|---|---|---|---|---|
| 1 | BzO-cyclohexane epoxide | p-TsOH | 0.2 | 93 | 90(99)(R)[f] | 89 |
| | | silica gel | 12 | 92 | 91(S) | 83 |
| | | YbCl₃ | 0.5 | 92 | 88(S) | 73 |
| | | AlMe₃ | 0.1 | 91 | 87(S) | 85 |
| 2 | p-CH₃—BzO-cyclohexane epoxide | p-TsOH | 0.1 | 93 | 93(99)(R)[f] | 70 |
| | | silica gel | 19 | 93 | 88(S) | 87 |
| | | AlMe₃ | 0.1 | 91 | 85(S) | 85 |
| 3 | Me₃CCOO-cyclohexane epoxide | p-TsOH | 0.3 | 92 | 87(99)(R)[f] | 72 |
| | | silica gel | 12 | 92 | 90(S) | 95 |
| | | YbCl₃ | 0.5 | 92 | 94(S) | 79 |
| | | AlMe₃ | 0.2 | 92 | 89(S) | 90 |
| 4 | BzO-cycloheptane epoxide | p-TsOH | 0.3 | 97 | 97(R)[g] | 77 |
| | | silica gel | 48 | 97 | 97(S) | 70 |
| | | YbCl₃ | 0.3 | 97 | 96(S) | 84 |
| | | AlMe₃ | 0.2 | 97 | 69(S) | 91 |
| 5[l] | BzO-cyclooctane epoxide | p-TsOH | 2 | 94 | 90(99)(R)[h] | 68 |
| | | YbCl₃ | 3 | 94 | 77(S) | 87 |
| | | AlMe₃[b] | 0.1 | 94 | 69(S) | 79 |
| 6[l] | Ph/AcO/CH₃ epoxide | p-TsOH | 0.3 | 94 | 94(R)[i] | 72 |
| | | AlMe₃[c] | 5 | 94 | 90(R) | 71 |
| 7 | BzO-tetrahydronaphthalene epoxide | p-TsOH | 0.05 | 99 | 99(R)[g] | 79 |
| | | silica gel | 48 | 99 | 38(R) | 45[k] |
| | | YbCl₃ | 2.5 | 99 | 57(R) | 87 |
| | | AlMe₃ | 0.1 | 99 | 93(R) | 81 |

[a]All reactions were carried out at room temperature with 10 mol % p-TsOH (dried by azeotropic removal of its hydrate) in dry CH₃NO₂, or 5–10 times (by weight) silica gel (Davisil 35-60 mesh, pH 7.0) in CH₃NO₂, or 10 mol % YbCl₃ in CH₂Cl₂, or 10 mol % AlMe₃ in CH₃NO₂ unless otherwise noted.
[b]100 mol % AlMe₃ was used.
[c]20 mol % AlMe₃ was used.
[d]Enantioselectivity was determined by chiral HPLC (Chiralcel OD) except entries 3 and 6 where enantioselectivity was determined by ¹H NMR shift analysis with Eu(hfc)₃. For determining absolute configuration of these epoxides see Zhu et al., Tetrahedron Lett. 1998, 39, 7819–7822.
[e]Enantioselectivity was determined by chiral HPLC (Chiralcel OD) except entry 3 where enantioselectivity was determined by ¹H NMR shift analysis with Eu(hfc)₃. The values in parentheses are the ee's after recrystallization.
[f]The absolute configurations were determined by comparing HPLC chromatograms (entries 1 and 2) or ¹H NMR shift analysis using Eu(hfc)₃ (entry 3) with the authentic sample prepared from commercially available (R,R)-1,2-trans-cyclohexanediol.
[g]The α-acyloxy ketones were hydrolyzed to α-hydroxy ketones and the absolute configurations were determined by comparing the measured optical rotations of the α-hydroxy ketones with the literature (see Nicolosi et al., Tetrahedron: Asymmetry 1995, 6, 519–524; and Naemura et al., Tetrahedron: Asymmetry 1997, 8, 2585–2595).
[h]The absolute configuration was tentatively assigned by analogy.
[i]The absolute configuration was determined by comparing the measured optical rotation with the literature (see Enders et al., Tetrahedron Lett. 1988, 29, 2437–2440).
[j]Isolated yield.
[k]Conversion determined by the ¹H NMR of the crude reaction mixture.
[l]No reaction was found with silica gel.

Thus, methods of the present invention also provide the flexibility to synthesize either enantiomer of α-acyloxy carbonyl compound from one enantiomer of an enol ester epoxide by judicious choice of reaction conditions, e.g., see Scheme 2.

Scheme 2

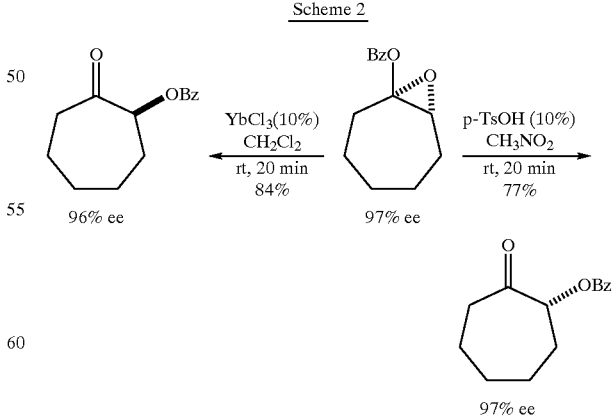

Another embodiment of the present invention provides a method for resolving a stereoisomeric, preferably racemic, mixture (i.e., a kinetic resolution) of an enol ester epoxide, e.g., a method for producing an enantiomerically enriched mixture of an enol ester epoxide from a stereochemical mixture of the enol ester epoxide. Preferably, the kinetic resolution comprises contacting the stereochemical mixture of the enol ester epoxide with a chiral Lewis acid catalyst, which are discussed above, to convert predominantly one enantiomer of the enol ester epoxide to an α-acyloxy carbonyl compound. Preferably, the kinetic resolution of the enol ester epoxide to the α-acyloxy carbonyl compound is stereoselective. More preferably, the kinetic resolution of the enol ester epoxide comprises producing the α-acyloxy carbonyl compound with predominantly inversion of stereochemistry. This embodiment is based on the discovery by the present inventors that certain chiral Lewis acids can catalyze the rearrangement of enol ester epoxides stereoselectively, thereby allowing kinetic resolution of racemic enol ester epoxides, as generally illustrated in Scheme 3 where LA* is a chiral Lewis acid.

Scheme 3

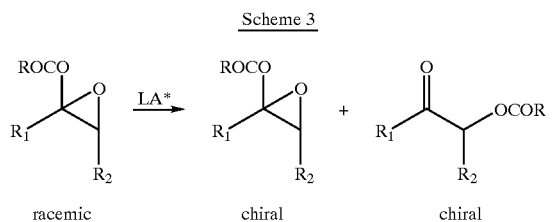

racemic      chiral      chiral

As stated above, using the disclosure of the present invention, one of ordinary skill in the art can readily determine appropriate chiral Lewis acid catalyst for kinetic resolution of enol ester epoxides. For example, using racemic 1-benzoyloxy-1,2-epoxycyclohexane 1 (Scheme 4), a variety of chiral Lewis acids can be tested for stereoselective kinetic resolution of the enol ester epoxide. In one aspect, BINOL-Ti(O$^i$Pr)$_4$ is a particularly useful chiral Lewis acid catalyst in stereoselectively resolving enol ester epoxides. Thus, as shown in Scheme 4, treating epoxide 1 with 5 mol % [(R)-BINOL]$_2$-Ti(O$^i$Pr)$_4$ (3) in Et$_2$O at 0° C. for 0.5 h led to a 52% conversion as determined by $^1$H NMR assay of the crude reaction mixture. Analysis of the unreacted epoxide and the rearranged product using chiral HPLC (Chiralcel OD) revealed a 99% ee for the epoxide and an 89% ee for 2-benzoyloxycyclohexanone (2). Both the recovered (i.e., unreacted or enriched) epoxide and the rearranged ketone were determined to be enriched in the R-isomer, revealing that the S-isomer of epoxide 1 had rearranged to the R-isomer of 2, i.e., the rearrangement occurred with inversion of configuration.

Scheme 4

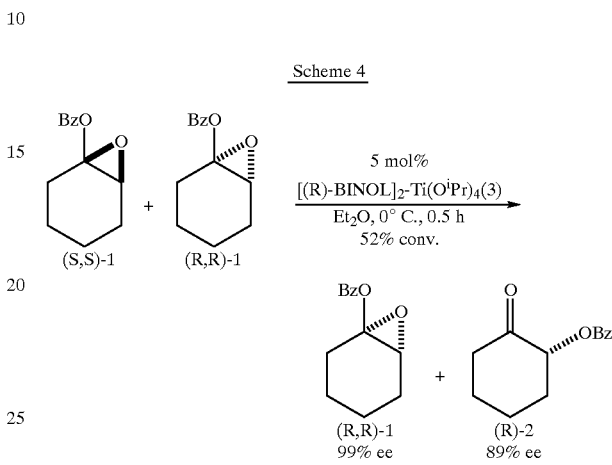

It is believed that the ratio of chiral ligand to metal is important both for the reactivity and selectivity. Preferably, methods of the present invention uses two or more equivalents of BINOL per Ti. In addition, while a variety of aprotic organic solvent may be used in a kinetic resolution of enol ester epoxides, Et$_2$O and CH$_2$Cl$_2$ are particularly preferred solvents.

Methods of the present invention are applicable to a wide variety of ester groups with different steric and electronic properties. For example, as shown in Table 3, a wide range of ester groups can be present in the enol ester epoxide.

TABLE 3

Kinetic Resolution of Enol Ester Epoxides Catalyzed by [(R)—BINOL]$_2$—Ti(O$^i$Pr)$_4$ [a]

| entry | substrate | time (h) | conv. (%)[b] | recov'd epoxide S.M. ee (%) | yield[c] (%) | product ee % | k$_{rel}$[d] (k$_f$/k$_s$) |
|---|---|---|---|---|---|---|---|
| 1[e] | R = Ph | 1.0 | 50 | 97[i](R)[m] | 34 | 90[i](R)[o] | >100 |
| 2 | R = p-CH$_3$Ph | 0.5 | 50 | 99[j] | 34 | 84[j](R)[o] | >100 |
| 3 | R = m-CH$_3$Ph | 0.4 | 53[h] | 97[j] | 36 | 87[j] | 55 |
| 4 | R = p-ClPh | 0.5 | 52 | 99[j] | 32 | 87[i](R)[o] | >100 |
| 5 | R = p-NO$_2$Ph | 2.2 | 49 | 96[j] | 39 | 96[i](R)[o] | >100 |
| 6 | R = 3,5-Me$_2$Ph | 0.6 | 53 | 99[k] | 35 | 83[j] | 80 |
| 7 | R = 2,6-Me$_2$Ph | 1.7 | 50 | 99[k] | 37 | 90[j] | >100 |

TABLE 3-continued
Kinetic Resolution of Enol Ester Epoxides Catalyzed by [(R)—BINOL]$_2$—Ti(O$^i$Pr)$_4$[a]
| entry | substrate | time (h) | conv. (%)[b] | recov'd epoxide S.M. ee (%) | yield[c] (%) | product ee % | $k_{rel}$[d] ($k_F/k_S$) |
|---|---|---|---|---|---|---|---|
| 8 | R = 1-Napth. | 0.9 | 52[h] | 98[k] | 33 | 91[j] | 91 |
| 9[e] | R = $^t$Bu | 0.6 | 54 | 97[l](R)[m] | 22 | 88[l](R)[o] | 43 |
| 10 | R = Me | 1.2 | 68 | 85[j](R)[m] |  | 48[j](R)[o] | 6 |
| 11[f] |  | 24 | 51[h] | 98[j] | 33 | 93[i] | >100 |
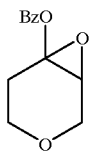
| 12 |  | 3.0 | 55 | 99[k](R)[m] | 33 | 89[i](R)[p] | 49 |
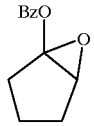
| 13 |  | 6.5 | 54 | 98[i](R)[m] | 34 | 80[i](R)[q] | 50 |
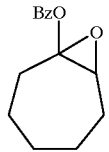
| 14[g] |  | 68.5 | 63 | 97[k](R)[m] | 32 | 71[k](R)[p] | 14 |
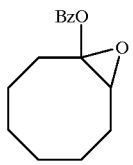
| 15 |  | 3.0 | 69 | 99[i](R)[n] | 30 | 50[i](R)[n] | 12 |
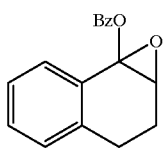

TABLE 3-continued

Kinetic Resolution of Enol Ester Epoxides
Catalyzed by [(R)—BINOL]$_2$—Ti(O$^i$Pr)$_4$$^a$

| entry | substrate | time (h) | conv. (%)$^b$ | S.M. ee (%) | recov'd epoxide yield$^c$ (%) | product ee % | k$_{rel}$$^d$ (k$_F$/k$_S$) |
|---|---|---|---|---|---|---|---|
| 16$^g$ | | 163 | 58 | 54$^i$ | | 38$^j$ | 4 |

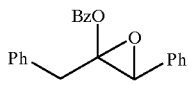

$^a$All reactions were carried out with substrate (0.5 mmol) and catalyst (5 mol %) in solvent (2 mL) at 0° C. unless otherwise noted.
$^b$The conversion was determined by $^1$H NMR of the crude reaction mixture after work-up.
$^c$Isolated yield.
$^d$The relative rate was calculated using the equation k$_{rel}$ = k$_F$/k$_s$ = ln[(1 − C)(1 − ee)] / ln[(1 − C)(1 + ee)] where C is the conversion and ee is the percent enantiomeric excess of the recovered starting material (see Kagan et al., Top. Stereochem. 1988, 18, 249).
$^e$2.5 mol % catalyst used.
$^f$10 mol % catalyst used.
$^g$20 mol % catalyst used. For entry 16, the reaction was carried out at room temperature.
$^h$The conversion was calculated applying the ee's of the recovered starting material and the product to the following equation: ee(SM) / ee(product) = C / (1 − C).
$^i$Enantioselectivity was determined by chiral HPLC (Chiralcel OD).
$^j$Enantioselectivity was determined by chiral HPLC (Chiralpak AD).
$^k$Enantioselectivity was determined by chiral HPLC (Chiralcel OJ).
$^l$Enantioselectivity was determined by $^1$H NMR shift analysis with Eu(hfc)$_3$.
$^m$The absolute configurations were assigned by comparing the measured optical rotations with the epoxides obtained by asymmetric epoxidation (see Zhu et al., Tetrahedron Lett. 1998, 39, 7819).
$^n$The absolute configurations were assigned by comparing HPLC chromatograms with the enol ester epoxide obtained by asymmetric epoxidation (see Zhu et al., Tetrahedron Lett. 1998, 39, 7819) and the α-benzoyloxy ketone obtained from a stereospecific rearrangement of the chiral enol ester epoxide (see Zhu et al., J. Am. Chem. Soc. 1999, 121, 4080).
$^o$The absolute configurations were determined by comparing the measured optical rotations with the authentic samples prepared from commercially available (R,R)-1,2-trans-cyclohexanediol.
$^p$The absolute configurations were assigned based on the epoxide configurations and the mechanistic deduction from the transformations of Scheme 5.
$^q$The absolute configuration was determined by comparing the measured optical rotation with the reported one (see Zhu et al., J. Am. Chem. Soc. 1999, 121, 4080).

Methods of the present invention is applicable to a variety of enol ester epoxides containing a variety of carbocyclic ring systems, including 5, 6, 7, and 8-membered ring systems (Table 3, entries 1–14). Moreover, methods of the present invention provides recovery of enol ester epoxides with high enantiomeric excess. Furthermore, substantially pure epoxides can be isolated in reasonable yields. It has been found by the present inventors that compared to the other ring systems, the 8-membered system appeared to be substantially less reactive, thereby requiring more catalyst and a longer reaction time. In contrast to the cyclic epoxides, kinetic resolution of acyclic epoxides appeared to be less effective (Table 3, entry 16).

As discussed above (Scheme 4), methods of the present invention provides rearrangements, i.e., conversion of enol ester epoxide to α-acyloxy carbonyl compound, with inversion of configuration, i.e., stereochemistry. As a result, the remaining epoxide and the rearranged α-acyloxy ketone have the same configuration at C$_2$ carbon atom.

Methods of the present invention can also include further converting the remaining epoxide to the rearranged α-acyloxy ketone using an achiral acid. In one aspect, rearrangement of the remaining enol ester epoxide is conducted with an achiral acid catalyst which is capable of catalyzing the rearrangement with retention of configuration. In this manner a high yield (>50%) of enantiomerically enriched α-acyloxy ketone can be obtained. For example, after the kinetic resolution reaction of 1-benzoyloxy-1,2-epoxycyclohexane 1 (Scheme 4), removal of the chiral catalyst by a filtration through a plug of silica gel, and treating the resulting mixture with 10% p-TsOH at room temperature for 20 min. gave 2-benzoyloxycyclohexanone in 78% overall isolated yield with 93% ee (Scheme 5). The % ee could be further enhanced to >99% by a single recrystallization from Et$_2$O. In this manner, both stereoisomers of enol ester epoxides in a racemic mixture can be stereoselectively converted to an enantiomerically enriched α-acyloxy carbonyl compound using a catalytic amount of a chiral Lewis acid followed by a catalytic amount of an achiral acid.

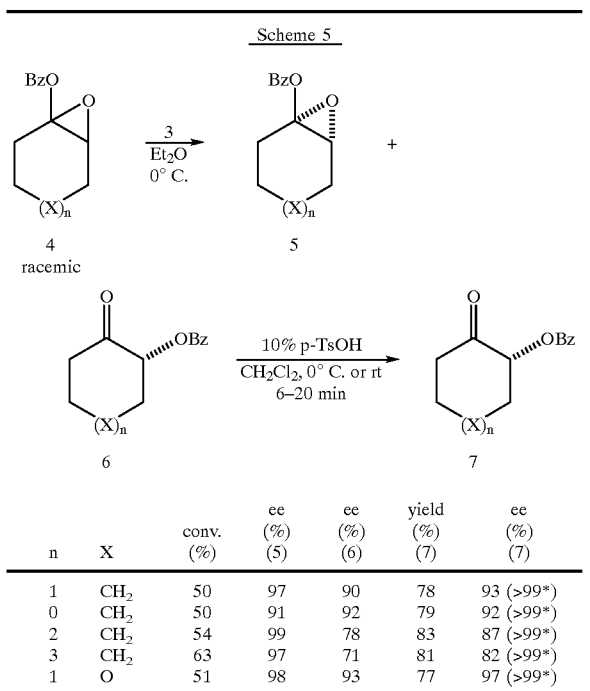

Scheme 5

| n | X | conv. (%) | ee (%) (5) | ee (%) (6) | yield (%) (7) | ee (%) (7) |
|---|---|---|---|---|---|---|
| 1 | CH$_2$ | 50 | 97 | 90 | 78 | 93 (>99*) |
| 0 | CH$_2$ | 50 | 91 | 92 | 79 | 92 (>99*) |
| 2 | CH$_2$ | 54 | 99 | 78 | 83 | 87 (>99*) |
| 3 | CH$_2$ | 63 | 97 | 71 | 81 | 82 (>99*) |
| 1 | O | 51 | 98 | 93 | 77 | 97 (>99*) |

*the ee's after recrystallization

Alternatively, the remaining (i.e., enantiomerically enriched) enol ester epoxide can be separated and converted to the α-acyloxy carbonyl compound with inversion of stereochemistry, thereby providing methods for producing two separate and isomeric enantiomerically enriched α-acyloxy carbonyl compounds from a single racemic mixture of enol ester epoxides.

Additional objects, advantages, and novel features of this invention will become apparent to those skilled in the art upon examination of the following examples thereof, which are not intended to be limiting.

EXAMPLE

Enantiomerically enriched enol ester epoxides can be prepared by the procedures disclosed in, for example, Tu et al., *J. Am. Chem. Soc.* 1996, 118, 9806–9807; Wang et al., *J. Am. Chem. Soc.* 1997, 119, 11224–11235; and Zhu et al., *Tetrahedron Lett.* 1998, 39, 7819–7822.

Example 1

This example illustrates a representative procedure for acid-catalyzed rearrangement of enol ester epoxides.
p-TsOH as Catalyst:

To a solution of (1R,2R)-2-benzoyloxy-1,2-epoxycyclohexane (0.030 g, 0.137 mmol, 93% ee) in anhydrous nitromethane (0.4 mL) was added p-TsOH (0.0024 g, 0.0137 mmol). Upon stirring at room temperature for 10 min, the reaction mixture was quenched with saturated NaHCO$_3$ solution, extracted with ether, dried over anhydrous Na$_2$SO$_4$, filtered, concentrated, and purified on buffered silica gel (0.5–1% Et$_3$N) by flash column chromatography [EtOAc-CH$_2$Cl$_2$-hexane (3:7:40)] to afford (R)-2-benzoyloxy cyclohexanone (0.0267 g, 89% yield, 90% ee).
YbCl$_3$ as Catalyst:

To a solution of (1R,2R)-2-benzoyloxy-1,2-epoxycyclohexane (0.030 g, 0.137 mmol, 93% ee) in anhydrous CH$_2$Cl$_2$ (0.4 mL) was added YbCl$_{13}$ (0.0048 g, 0.0137 mmol). Upon stirring at room temperature for 30 min, the reaction mixture was quenched with saturated NaHCO$_3$ solution, extracted with ether, dried over anhydrous Na$_2$SO$_4$, filtered, concentrated, and purified on buffered silica gel (0.5–1% Et$_3$N) by flash column chromatography [EtOAc-CH$_2$Cl$_2$-hexane (3:7:40)] to afford (S)-2-benzoyloxy cyclohexanone (0.022 g, 73% yield, 88% ee).

Example 2

This example illustrates a representative procedure for kinetic resolution of enol ester epoxide using the process of the present invention.
A. Preparation of Enantiomerically Enriched Enol Ester Epoxide
(note: the reaction is moisture sensitive and needs to be carried out under rigorously anhydrous conditions).

To a solution of (R)-(+)-binaphthol (7.9 mg, 0.0275 mmol) in CH$_2$Cl$_2$ (0.5 mL) was added a solution of Ti(O$^i$Pr)$_4$ (3.8 μL, 3.6 mg, 0.0125 mmol) in CH$_2$Cl$_2$ (0.5 mL). Upon stirring at room temperature for 5–10 h, the reaction mixture was concentrated and dried using a vacuum pump (ca. 0.5 h). The catalyst was then dissolved in Et$_2$O (1 mL) and cooled in an ice bath. To this solution was added a solution of racemic 1-benzoyloxy-1,2-epoxycyclohexane (0.109 g, 0.5 mmol) in Et$_2$O (1 mL). After stirring at 0° C. for 1 h, the reaction mixture was quenched with saturated NaHCO$_3$ solution (4 mL) and poured into a mixture of ether (20 mL) and saturated NaHCO$_3$ solution (10 mL). The organic layer was washed with water and brine, dried (Na$_2$SO$_4$) (ca. 10 min), and rapidly filtered through a plug of silica gel (ca. 10 g) (pre-treated with 5% Et$_3$N in hexane and washed thoroughly with hexane to remove Et$_3$N before use). The silica gel was further washed with Et$_2$O (10 mL). The combined ether solutions were concentrated to give a mixture of (R)-1-benzoyloxy-1,2-epoxycyclohexane and (R)-2-benzoyloxycyclohexanone. After a sample was taken for the determination of the conversion and ee's, the mixture was purified by flash chromatography (silica gel was pre-treated with 5% Et$_3$N) using hexane-CH$_2$Cl$_2$-EtOAc (84:10:6) as eluent to afford (R)-1-benzoyloxy-1,2-epoxycyclohexane as a colorless oil (0.0365 g, 34% yield, 98% ee).
B. Preparation of Enantiomerically Enriched α-Acyloxy Ketone
(note: the reaction is moisture sensitive and needs to be carried out under rigorously anhydrous conditions).

To a solution of (R)-(+)-binaphthol (7.9 mg, 0.0275 mmol) in CH$_2$Cl$_2$ (0.5 mL) was added a solution of Ti(O$^i$Pr)$_4$ (3.8 uL, 3.6 mg, 0.0125 mmol) in CH$_2$Cl$_2$ (0.5 mL). Upon stirring at room temperature for 5–10 h, the reaction mixture was concentrated and dried using a vacuum pump (ca. 0.5 h). The catalyst was then dissolved in Et$_2$O (1 mL) and cooled in an ice bath. To this solution was added a solution of racemic 1-benzoyloxy-1,2-epoxycyclohexane (0.109 g, 0.5 mmol) in Et$_2$O (1 mL). After stirring at 0° C. for 1 h, the reaction mixture was quenched with saturated NaHCO$_3$ solution (4 mL) and poured into a mixture of ether (20 mL) and saturated NaHCO$_3$ solution (10 mL). The organic layer was washed with water and brine, dried (Na$_2$SO$_4$), and rapidly filtered through a plug of silica gel (ca. 10 g) (pre-treated with 5% Et$_3$N in hexane and washed thoroughly with hexane to remove Et$_3$N before use). The silica gel was further washed with Et$_2$O (10 mL). The combined ether solutions were concentrated to give a residue. Upon drying under vacuum for 1 h, the mixture was dissolved in CH$_2$Cl$_2$ (4 mL) followed by addition of anhydrous p-TsOH (8.6 mg, 0.05 mmol). After stirring at room temperature for 20 min, the mixture was rapidly filtered through a plug of silica gel (ca. 10 g) (without Et$_3$N treatment) followed by washing with ether (2×10 mL). The combined solutions were concentrated to give (R)-2-benzoyloxycyclohexanone as a white solid (0.0845 g, 78% yield, 93% ee).

1-Benzoyloxy-1,2-epoxycyclohexane (Table 3, entry 1).
Colorless oil; [α]$^{25}$D=−36.3 (c 0.49, CHCl$_3$) (98% ee).

1-(p-Methylbenzoyloxy)-1,2-epoxycyclohexane (Table 3, entry 2).
White solid; [α]$^{25}_D$=−30.7 (c 0.45, CHCl$_3$) (99% ee).

1-(m-Methylbenzoyloxy)-1,2-epoxycyclohexane (Table 3, entry 3).
Colorless oil; [α]$^{25}_D$=−31.3 (c 0.44, CHCl$_3$) (97% ee); IR (NaCl) 1725 cm$^{-1}$; $^1$H NMR δ 7.86–7.79 (m, 2H), 7.40–7.28 (m, 2H), 3.41 (m, 1H), 2.39 (s, 3H), 2.34 (dt, J=14.4, 6.6 Hz, 1H), 2.22 (dt, J=14.4, 6.3 Hz, 1H), 2.07–1.86 (m, 2H), 1.58–1.49 (m, 2H), 1.48–1.38 (m, 2H); $^{13}$C NMR δ 165.5, 138.4, 134.3, 130.4, 129.5, 128.5, 127.1, 83.6, 59.6, 28.4, 25.0, 21.5, 20.6, 19.1; Anal. Calcd. for C$_{14}$H$_{16}$O$_3$: C, 72.38; H, 6.95. Found: C, 72.39; H. 6.96.

1-(p-Chlorobenzoyloxy)-1,2-epoxycyclohexane (Table 3, entry 4).
White solid; [α]$^{25}_D$=−28.9 (c 0.67, CHCl$_3$) (99% ee); IR (NaCl) 1728, 1594 cm$^{-1}$; $^1$H NMR δ 7.92 (dt, J=8.4, 2.1 Hz, 2H), 7.37 (dt, J =8.4, 2.1 Hz, 2H), 3.38 (s, 1H), 2.32 (dt, J=14.1, 6.9 Hz, 1H), 2.17 (dt, J=14.1, 6.1 Hz, 1H), 2.03–1.87 (m, 2H), 1.51–1.37 (m, 4H); $^{13}$C NMR δ 164.5, 140.1, 131.3, 129.0, 128.1, 83.9, 59.5, 28.3, 24.8, 20.5, 19.0; Anal. Calcd. for C$_{13}$H$_{13}$O$_3$Cl: C, 61.79; H, 5.19. Found: C, 61.81; H, 5.47.

1-(p-Nitrobenzoyloxy)-1,2-epoxycyclohexane (Table 1, entry 5).
Off-white solid; [α]$^{25}_D$=−29.8 (c 0.45, CHCl$_3$) (99% ee); IR (NaCl) 1714, 1527 cm$^{-1}$; $^1$H NMR δ 8.30 (dt, J=8.8, 1.8 Hz, 2H), 8.20 (dt J=8.8, 1.8 Hz, 2H), 3.45 (m, 1H), 2.40 (dt, J=14.2, 6.6 Hz, 1H), 2.22 (dt, J=14.2, 6.6 Hz, 1H), 2.00 (m, 2H), 1.61–1.40 (m, 4H); $^{13}$C NMR δ 163.3, 150.8, 134.8, 130.9, 123.6, 84.3, 59.3, 28.1, 24.7, 20.4, 18.9; Anal. Calcd. for C$_{13}$H$_{13}$NO$_5$: C, 59.31; H, 4.98; N, 5.32. Found: C, 59.09; H, 5.18; N, 5.26.

1-(3,5-Dimethylbenzoyloxy)-1,2-epoxycyclohexane (Table 3, entry 6).
Colorless oil; [α]$^{25}_D$=−33.1 (c 0.36, CHCl$_3$) (99% ee); IR (NaCl) 1725 cm$^{-1}$; $^1$H NMR δ 7.64 (s, 2H), 7.20 (s, 1H), 3.41 (m, 1H), 2.35 (s, 6H), 2.33 (m, 1H), 2.21 (dt, J=14.1, 6.3 Hz, 1H), 2.02–1.95 (m, 2H), 1.59–1.50 (m, 2H), 1.47–1.40 (m, 2H); $^{13}$C NMR δ 168.7, 138.4, 135.3, 129.4, 127.7, 83.6, 59.7, 28.4, 24.9, 21.3, 20.5, 19.0; Anal. Calcd. for C$_{15}$H$_{18}$O$_3$: C, 73.13; H, 7.37. Found: C, 73.21; H, 7.17.

1-(2,6-Dimethylbenzoyloxy)-1,2-epoxycyclohexane (Table 3, entry 7).
Colorless oil; [α]$^{25}_D$=−12.0 (c 0.75, CHCl$_3$) (98% ee); IR (NaCl) 1736 cm$^{-1}$; $^1$H NMR δ 7.18 (t, J=7.2 Hz, 1H), 7.01 (d, J=7.2 Hz, 2H), 3.44 (m, 1H), 2.43 (m, 1H), 2.33 (s, 6H), 2.30 (m, 1H), 2.10–1.90 (m, 2H), 1.60–1.52 (m, 2H), 1.49–1.41 (m, 2H); $^{13}$C NMR δ 168.6, 135.0, 129.7, 128.1, 127.8, 83.7, 59.5, 28.4, 24.9, 20.6, 19.9, 19.1; Anal. Calcd. for C$_{15}$H$_{18}$O$_3$: C, 73.13; H, 7.37. Found: C, 73.32; H, 7.22.

1-(1-Naphthoyloxy)-1,2-epoxycyclohexane (Table 3, entry 8).
White solid; [α]$^{25}_D$=−42.3 (c 0.22, CHCl$_3$) (98% ee); IR (NaCl) 1720 cm$^{-1}$; $^1$H NMR δ 8.98 (d, J=9.0 Hz, 1H), 8.25 (dd, J=7.2, 1.0 Hz, 1H), 8.04 (d, J=8.4 Hz, 1H), 7.88 (d, J=8.4 Hz, 1H), 7.63 (m, 1H), 7.58–7.45 (m, 2H), 3.52 (m, 1H), 2.44 (dt, J=14.1, 6.6 Hz, 1H), 2.31 (dt, J=14.1, 6.3 Hz, 1H), 2.14–1.94 (m, 2H), 1.65–1.54 (m, 2H), 1.53–1.43 (m, 2H); $^{13}$C NMR δ 166.2, 134.3, 131.7, 131.2, 128.8, 128.3, 126.5, 125.9, 125.8, 124.6, 83.8, 59.7, 28.5, 25.0, 20.6, 19.1; Anal. Calcd. for C$_{17}$H$_{16}$O$_3$: C, 76.09; H, 6.01. Found: C, 76.18; H. 6.09.

1-Pivaloyloxy-1,2-epoxycyclohexane (Table 3, entry 9).
Colorless oil; [α]$^{25}_D$=−42.4 (c 0.50, CHCl$_3$) (97% ee).

1-Acetoxy-1,2-epoxycyclohexane (Table 3, entry 10).
Colorless oil; IR (NaCl) 1747, 1231 cm$^{-1}$; $^1$H NMR δ 3.30 (ddd, J=2.7, 1.8, 0.9 Hz, 1H), 2.24 (dtd, J=14.5, 6.6, 0.9 Hz, 1H), 2.11 (m, 1H), 2.06 (s, 3H), 1.92 (m, 2H), 1.51–1.32 (m, 4H); $^{13}$C NMR δ 169.7, 83.0, 59.4, 28.1, 24.8, 21.3, 20.4, 18.9; Anal. Calcd. for C$_8$H$_{12}$O$_3$: C, 61.52; H, 7.74. Found: C, 61.72;H, 8.11.

4-Benzoyloxy-3,4-epoxytetrahydro-4H-pyran (Table 3, entry 11).
White solid; [α]$^{25}_D$=−51.2 (c 0.60, CHCl$_3$) (99% ee); IR (NaCl) 1728 cm$^{-1}$; $^1$H NMR δ 8.04 (m, 2H), 7.60 (tt, J=7.2, 1.5 Hz, 1H), 7.46 (m, 2H), 4.09 (dd, J=13.5, 2.4 Hz, 1H), 3.98 (d, J=13.5 Hz, 1H), 3.67 (m, 2H), 3.48 (d, J=2.4 Hz, 1H), 2.55 (dt, J=14.4, 6.0 Hz, 1H), 2.32 (dt, J=14.4, 5.4 Hz, 1H); $^{13}$C NMR 133.9, 130.0, 129.1, 128.7, 81.0, 65.0, 62.6, 56.9, 29.3; Anal. Calcd. for C$_{12}$H$_{12}$O$_4$: C, 65.43; H, 5.50. Found: C,65.30; H. 5.37.

1-Benzoyloxy-1,2-epoxycyclopentane (Table 3, entry 12).
Colorless oil; [α]$^{25}_D$=−31.7 (c 0.55, CHCl$_3$) (99% ee); IR (NaCl) 1722, 1272 cm$^{-1}$; $^1$H NMR δ 8.02 (m, 2H), 7.57 (tt, J=7.5, 1.2 Hz, 1H), 7.43 (m, 2H), 3.78 (s, 1H), 2.43 (dd, J=13.2, 8.4 Hz, 1H), 2.11 (ddd, J=13.2, 9.9, 9.0 Hz, 1H), 2.02–1.70 (m, 3H), 1.54 (m, 1H); $^{13}$C NMR δ 165.2, 133.8, 130.1, 129.3, 128.7, 90.0, 62.8, 28.4, 6.3, 20.2; Anal. Calcd. for C$_{12}$H$_{12}$O$_3$: C, 70.57; H, 5.92. Found: C, 70.35; H, 6.00.

1-Benzoyloxy-1,2-epoxycycloheptane (Table 3, entry 13).
White solid; [α]$^{25}_D$=−32.8 (c 0.50, CHCl$_3$) (98% ee).

1-Benzoyloxy-1,2-epoxycyclooctane (Table 3, entry 14).
White solid; [α]$^{25}_D$=+9.3 (c 0.31, CHCl$_3$) (98% ee).

2-Benzoyloxy-1,3-diphenyl-1,2-epoxypropane (Table 3, entry 16).
White solid; IR (NaCl) 1729 cm$^{-1}$; $^1$H NMR δ 7.78 (m, 2H), 7.50 (m, 1H), 7.39–7.26 (m, 9H), 7.21–7.16 (m, 3H), 3.95 (s, 1H), 3.71 (d, J=14.7 Hz, 1H), 3.52 (d, J=14.7 Hz, 1H); $^{13}$C NMR δ 164.7, 133.5, 133.0, 130.3, 129.8, 129.2, 128.7, 128.5, 128.4, 128.1, 127.4, 127.1, 88.2, 62.4, 39.4; Anal. Calcd. for C$_{22}$H$_{18}$O$_3$: C, 79.97, H, 5.50. Found: C, 80.17; H, 5.55.

2-Benzoyloxycyclohexanone (Table 3, entry 1).
White solid; mp 81–83° C.; [α]$^{25}_D$=+18.4 (c 0.43, CHCl$_3$) (93% ee).

2-(p-Methylbenzoyloxy)cyclohexanone (Table 3, entry 2).
White solid; mp 68–69° C.; [α]$^{25}_D$=+9.7 (c 0.48, CHCl$_3$) (91% ee).

2-(m-Methylbenzoyloxy)cyclohexanone (Table 3, entry 3).
White solid; mp 73–74° C.; [α]$^{25}_D$=+13.2 (c 0.41, CHCl$_3$) (92% ee); IR (NaCl): 1718 cm$^{-1}$; $^1$H NMR δ 7.92–7.86 (m, 2H), 7.40–7.30 (m, 2H), 5.41 (dd, J=11.4, 6.0 Hz, 1H), 2.62–2.42 (m, 3H), 2.40 (s, 3H), 2.19–1.58 (m, 5H); $^{13}$C NMR δ 204.4, 165.8, 138.2, 136.6, 134.0, 130.4, 128.3, 127.1, 77.1, 41.0, 33.4, 27.4, 24.0, 21.5; Anal. Calcd. for C$_{14}$H$_{16}$O$_3$: C, 72.38; H, 6.95. Found: C, 72.51; H, 6.84.

2-(p-Chlorobenzoyloxy)cyclohexanone (Table 3, entry 4).
White solid; mp 84–85° C.: [α]$^{25}_D$=+15.0 (c 0.46, CHCl$_3$) (89% ee); IR (NaCl) 1717, 1593, 1271 cm$^{-1}$; $^1$H NMR δ 8.03 (m,2H), 7.42 (m, 2H), 5.40 (dd, J=11.8, 6.3 Hz, 1H), 2.62–2.39 (m, 3H), 2.21–1.61 (m, 5H); $^{13}$C NMR δ 204.3, 164.9, 139.8, 131.4, 128.9, 128.3, 77.4, 40.9, 33.3, 27.4, 24.0; Anal. Calcd. for C$_{13}$H$_{13}$O$_3$Cl: C, 61.79; H, 5.19. Found: C, 61.42; H,5.58.

2-(p-Nitrobenzoyloxy)cyclohexanone (Table 3, entry 5).
White solid; mp 124–125° C.; [α]$^{25}_D$=+23.5 (c 0.43, CHCl$_3$) (94% ee); IR (NaCl) 1732, 1712, 1273 cm$^{-1}$; $^1$H NMR δ 8.23–8.32 (m, 4H), 5.43 (dd, J=11.8, 6.4 Hz, 1H), 2.64–2.42 (m, 3H), 2.21–1.63 (m, 5H); $^{13}$C NMR δ 203.8, 163.9, 150.8, 135.3, 131.2, 123.7, 78.0, 40.9, 33.2, 27.3, 24.0; HRMS Calcd. for $C_{13}H_{14}NO_5$ (M$^+$+1) 264.0872. Found 264.0877.

2-(3,5Dimethylbenzoyloxy)cyclohexanone (Table 3, entry 6).

White solid; mp 65–66° C.; $[\alpha]^{25}_D$=+6.5 (c 0.87, CHCl$_3$) (92% ee); IR (NaCl) 1717 cm$^{-1}$; $^1$H NMR δ 7.71 (s, 2H), 7.19 (s, 1H), 5.40 (dd, J=12.0, 6.3 Hz, 1H), 2.60–2.36 (m, 3H), 2.35 (s, 6H), 2.20–1.57 (m, 5H); $^{13}$C NMR δ 204.5, 166.0, 138.1, 134.9, 129.6, 127.6, 77.0, 41.0, 33.4, 27.5, 24.0, 21.3; Anal. Calcd. for $C_{15}H_{18}O_3$ C, 73.13; H, 7.37. Found: C, 72.91; H, 7.25.

2-(2,6-Dimethylbenzoyloxy)cyclohexanone (Table 3, entry 7).

White solid; mp 82–83° C.; $[\alpha]^{25}_D$=+23.0 (c 1.12, CHCl$_3$) (85% ee); IR (NaCl) 1727 cm$^{-1}$; $^1$H NMR δ 7.18 (t, J=7.6 Hz, 1H), 7.04 (d, J=7.6 Hz, 2H), 5.42 (dd, J=12.0, 6.0 Hz, 1H), 2.63–2.32 (m, 31), 2.42 (s, 6H), 2.24–1.55 (m, 5H); $^{13}$C NMR δ 204.0, 168.8, 135.5, 133.2, 129.6, 127.7, 77.0, 41.0, 33.3, 27.3, 24.0, 20.0; Anal. Calcd. for $C_{15}H_{18}O_3$: C, 73.13; H, 7.37. Found: C, 73.33; 7.14.

2-(1-Naphthoyloxy)cyclohexanone (Table 3, entry 8).

White solid; mp 94–95° C.; $[\alpha]^{25}_D$=+29.4 (c 0.50, CHCl$_3$) (95% ee); IR (NaCl) 1713 cm$^{-1}$; $^1$H NMR δ 8.91 (d, J=8.1 Hz, 1H), 8.27 (dd, J=7.2, 1.2 Hz, 1H), 8.02 (d, J=8.1 Hz, 1H), 7.87 (d, J=7.8 Hz, 1H), 7.64–7.47 (m, 3H), 5.53 (m, 1H), 2.64–2.40 (m, 3H), 2.18–1.62 (m, 5H); $^{13}$C NMR δ 204.7, 166.8, 133.9, 133.6, 131.5, 130.6, 128.6, 127.9, 127.0, 126.4, 126.0, 124.7, 77.3, 41.0, 33.4, 27.4, 24.0; Anal. Calcd. for $C_{17}H_{16}O_3$: C, 76.09; H, 6.01. Found: C, 75.99; H. 6.00.

2-Pivaloyloxycyclohexanone (Table 3, entry 9).

White solid; mp 35–36° C.; $[\alpha]^{25}_D$=+47.4 (c 0.49, CHCl$_3$) (92% ee).

2-Acetoxycyclohexanone (Table 3, entry 10).

Colorless liquid; IR (NaCl) 1732, 1721 cm$^{-1}$; $^1$H NMR δ 5.17 (dd, J=11.7, 6.3 Hz, 1H), 2.52 (dddd, J=13.2, 4.6, 2.6, 2.3 Hz, 1H), 2.41 (ddd, J=13.2, 6.0, 0.6 Hz, 1H), 2.31 (m, 1H), 2.16 (s, 3H), 2.14–1.92 (m, 2H), 1.54–1.85 (m, 3H); $^{13}$C NMR δ 204.7, 170.2, 76.7, 40.9, 33.2, 27.3, 23.9, 20.9.

3Benzoyloxy-tetrahydro-4H-pyran-4-one (Table 3, entry 11).

White solid; mp 76–77° C.; $[\alpha]^{25}_D$=+12.0 (c 0.75, CHCl$_3$) (97% ee); IR (NaCl) 1724 cm$^{-1}$; $^1$H NMR δ 8.07 (dd, J=8.4, 1.5 Hz, 2H), 7.59 (m, 1H), 7.45 (m, 2H), 5.52 (ddd, J=10.8, 6.9, 1.0 Hz, 1H), 4.46 (ddd, J=10.8, 6.9, 1.5 Hz, 1H), 4.32 (ddt, J=11.2, 7.2, 1.5 Hz, 1H), 3.73 (m, 2H), 2.85 (m, 1H), 2.60 (m, 1H); $^{13}$C NMR δ 200.6, 165.2, 133.7, 130.1, 129.2, 128.6, 74.2, 70.7, 68.7, 42.4; Anal. Calcd. for $C_{12}H_{12}O_4$: C, 65.43; H, 5.50. Found: C, 65.21; H, 5.49.

2-Benzoyloxycyclopentanone (Table 3, entry 12).

White solid; mp 87–88° C.: $[\alpha]^{25}_D$=−58.1 (c 0.73, CHCl$_3$) (92% ee); IR (NaCl) 1758, 1712 cm$^{-1}$; $^1$H NMR δ 8.06 (m, 2H), 7.57 (m, 1H), 7.44 (m, 2H), 5.31 (m, 1H), 2.61–2.28 (m, 3H), 2.22–1.85 (m, 3H); $^{13}$C NMR δ 212.3, 165.8, 133.4, 130.0, 129.5, 128.5, 76.3, 35.2, 28.8, 17.5; Anal. Calcd. for $C_{12}H_{12}O_3$: C, 70.57; H. 5.92. Found: C, 70.72; H, 6.02.

2-Benzoyloxycycloheptanone (Table 3, entry 13).

White solid; mp 59–60° C.; $[\alpha]^{25}_D$=−36.2 (c 0.60, CHCl$_3$) (87% ee).

2-Benzoyloxycyclooctanone (Table 3, entry 14).

White solid; mp 92–93° C.; $[\alpha]^{25}_D$=−33.9 (c 0.31, CHCl$_3$) (99% ee).

1-Benzoyloxy-1,3-diphenyl-2-propanone (Table 3, entry 16).

White solid; mp 56–57° C. (racemate); IR(NaCl) 1723 cm$^{-1}$; $^1$H NMR δ 8.09 (m, 2H), 7.56 (m, 1H), 7.38–7.49 (m, 7H), 7.29–7.19 (m, 3H), 7.06 (m, 2H), 6.30 (s, 1H), 3.80 (s, 2H); $^{13}$C NMR δ 201.4, 165.9, 133.6, 133.3, 133.0, 130.1, 129.8, 129.6, 129.4, 129.3, 128.7, 128.6, 128.5, 127.2, 80.8, 46.0; Anal. Calcd. for $C_{22}H_{18}O_3$: C, 79.97; H, 5.50. Found: C, 80.22; H, 5.62.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for stereoselectively producing an α-acyloxy carbonyl compound from an enol ester epoxide comprising contacting the enol ester epoxide with a chiral acid catalyst under conditions sufficient to stereoselectively produce the α-acyloxy carbonyl compound with inversion of stereochemistry.

2. The method of claim 1, wherein said acid catalyst is capable of converting the enol ester epoxide to the α-acyloxy carbonyl compound with inversion of stereochemistry.

3. The method of claim 2, wherein the enol ester epoxide is a racemic mixture.

4. The method of claim 3, wherein the chiral acid catalyst comprises a Lewis acid and a chiral ligand.

5. The method of claim 4, wherein the Lewis acid comprises a metal selected from the group consisting of transition metals, lanthanide metals, actinide metals, and mixtures thereof.

6. The method of claim 4, wherein the chiral ligand is selected from the group consisting of (R)-BINOL and (S)-BINOL.

7. The method of claim 4, wherein the chiral acid catalyst stereoselectively produces the α-acyloxy carbonyl compound with inversion of stereochemistry and enantiomerically enriched unreacted enol ester epoxide.

8. The method of claim 7, wherein said method further comprises contacting the enantiomerically enriched unreacted enol ester epoxide with a second acid catalyst to produce the α-acyloxy carbonyl compound with retention of stereochemistry.

9. The method of claim 2, wherein the enol ester epoxide is enantiomerically enriched.

10. The method of claim 9, wherein enantiomeric excess of the enol ester epoxide is at least about 80% ee.

11. The method of claim 1, wherein said method produces the α-acyloxy carbonyl compound in an enantiomeric excess of at least about 80% ee.

12. A method for stereoselectively producing an α-acyloxy carbonyl compound from a racemic mixture of enol ester epoxide comprising:

(a) contacting the enol ester epoxide with a chiral Lewis acid catalyst under conditions sufficient to stereoselectively produce the α-acyloxy carbonyl compound predominantly from one stereoisomer of the enol ester epoxide and enantiomerically enriched enol ester epoxide of the other stereoisomer; and (b) contacting the enantiomerically enriched enol ester epoxide with an acid catalyst under a condition sufficient to stereoselectively produce the α-acyloxy carbonyl.

13. The method of claim 12, wherein the chiral Lewis acid catalyst comprises a metal and a chiral ligand.

14. The method of claim 13, wherein the metal is selected from the group consisting of transition metals, lanthanide metals, actinide metals, and mixtures thereof.

15. The method of claim 13, wherein the chiral ligand is selected from the group consisting of (R)-BINOL and (S)-BINOL.

16. The method of claim 12, wherein the acid catalyst is selected from the group consisting of p-toluenesulfonic acid, silica gel, $AlMe_3$, $ErCl_3$, $YbCl_3$ and $Sn(OTf)_2$.

17. The method of claim 12, wherein at least one of the Lewis acid catalyst and the acid catalyst is capable of converting the enol ester epoxide to the α-acyloxy carbonyl compound with inversion of stereochemistry.

18. A method for stereoselectively producing an α-acyloxy carbonyl compound from an enantiomerically enriched enol ester epoxide comprising contacting the enol ester epoxide with a chiral acid catalyst under conditions sufficient to stereoselectively produce the α-acyloxy carbonyl compound with inversion of stereochemistry.

19. The method of claim 18, wherein the chiral acid catalyst is capable of converting the enol ester epoxide to the α-acyloxy carbonyl compound with inversion of stereochemistry.

20. A method for producing an enantiomerically enriched mixture of an enol ester epoxide from a stereochemical mixture of the enol ester epoxide, said method comprising contacting the stereochemical mixture of the enol ester epoxide with a chiral Lewis acid catalyst to convert predominantly one enantiomer of the enol ester epoxide to an α-acyloxy carbonyl compound.

21. The method of claim 20, wherein the chiral Lewis acid catalyst converts predominantly one enantiomer of the enol ester epoxide compound to an α-acyloxy carbonyl compound stereoselectively.

22. The method of claim 20, wherein the chiral Lewis acid catalyst is capable of converting the enol ester epoxide to the α-acyloxy carbonyl compound with inversion of stereochemistry.

23. The method of claim 22, wherein said method comprises producing the α-acyloxy carbonyl compound with predominantly inversion of stereochemistry.

24. The method of claim 23, wherein the chiral Lewis acid catalyst comprises a Lewis acid and a chiral ligand.

25. The method of claim 24, wherein the Lewis acid comprises a metal selected from the group consisting of transition metals, lanthanide metals, actinide metals, and mixtures thereof.

26. The method of claim 24, wherein the chiral ligand is selected from the group consisting of (R)-BINOL and (S)-BINOL.

* * * * *